(12) United States Patent
Cromwell

(10) Patent No.: US 11,918,408 B2
(45) Date of Patent: Mar. 5, 2024

(54) ENHANCED DETECTION AND ANALYSIS OF BIOLOGICAL ACOUSTIC SIGNALS

(71) Applicant: Entac Medical, Inc., Memphis, TN (US)

(72) Inventor: John W. Cromwell, Iowa City, IA (US)

(73) Assignee: Entac Medical, Inc., Memphis, TN (US)

( * ) Notice: Subject to any disclaimer, the term of this patent is extended or adjusted under 35 U.S.C. 154(b) by 43 days.

(21) Appl. No.: 16/851,085

(22) Filed: Apr. 16, 2020

(65) Prior Publication Data
US 2020/0330066 A1 Oct. 22, 2020

Related U.S. Application Data

(60) Provisional application No. 62/834,906, filed on Apr. 16, 2019.

(51) Int. Cl.
A61B 7/00 (2006.01)
A61B 5/00 (2006.01)

(52) U.S. Cl.
CPC ............ *A61B 7/008* (2013.01); *A61B 5/6823* (2013.01); *A61B 5/7203* (2013.01); *A61B 5/7275* (2013.01); *A61B 5/7405* (2013.01); *A61B 5/742* (2013.01); *A61B 5/746* (2013.01); *A61B 2503/40* (2013.01)

(58) Field of Classification Search
CPC ..... A61B 7/008; A61B 5/6823; A61B 5/7203; A61B 5/7275; A61B 5/7405; A61B 5/742; A61B 5/746; A61B 5/4255; A61B 5/073; A61B 5/076; A61B 5/42; A61B 7/20; G16H 50/20; G16H 50/03
See application file for complete search history.

(56) References Cited

U.S. PATENT DOCUMENTS

| 5,140,994 | A | 8/1992 | Campbell et al. |
| 5,301,679 | A | 4/1994 | Taylor |
| 5,853,005 | A | 12/1998 | Scanlon |
| 6,056,703 | A | 5/2000 | Sandler et al. |
| 6,228,040 | B1 * | 5/2001 | Craine ................... A61B 7/008 600/586 |
| 6,287,266 | B1 | 9/2001 | Sandler et al. |

(Continued)

FOREIGN PATENT DOCUMENTS

| CN | 101541372 | 9/2009 |
| CN | 104305961 A | 1/2015 |

(Continued)

OTHER PUBLICATIONS

Chinese Search Report and English Language translation issued in related application No. CN 201180024426.5, dated Apr. 21, 2014.

(Continued)

*Primary Examiner* — Matthew Kremer
*Assistant Examiner* — Kyle W. Kretzer
(74) *Attorney, Agent, or Firm* — Arnall Golden Gregory LLP

(57) ABSTRACT

Devices and methods for predicting risk and likelihood of post-operative gastrointestinal impairment based on regression analysis of multiple spectral events related to intestinal sounds, with decreased or eliminated falsely elevated values of those events due to ambient noise.

20 Claims, 18 Drawing Sheets

(56) References Cited

U.S. PATENT DOCUMENTS

| | | | |
|---|---|---|---|
| 6,425,874 B1 | 7/2002 | Sandler et al. | |
| 6,520,924 B2 | 2/2003 | Lee | |
| 6,572,560 B1 | 6/2003 | Watrous et al. | |
| 6,629,937 B2 | 10/2003 | Watrous | |
| 6,776,766 B2 | 8/2004 | Sandler et al. | |
| 6,840,913 B2* | 1/2005 | Mansy | A61B 7/008 600/593 |
| 8,715,201 B2 | 5/2014 | Koehler et al. | |
| 9,179,887 B2 | 11/2015 | Cromwell | |
| 10,603,006 B2 | 3/2020 | Cromwell | |
| 2002/0052559 A1 | 5/2002 | Watrous | |
| 2002/0058889 A1 | 5/2002 | Lee | |
| 2002/0156398 A1 | 10/2002 | Mansy et al. | |
| 2004/0032957 A1* | 2/2004 | Mansy | A61B 7/04 381/67 |
| 2006/0025650 A1 | 2/2006 | Gavriely | |
| 2007/0282174 A1 | 12/2007 | Sabatino | |
| 2008/0235016 A1 | 9/2008 | Paul et al. | |
| 2008/0306355 A1 | 12/2008 | Walker | |
| 2010/0010358 A1 | 1/2010 | Boute et al. | |
| 2010/0172839 A1 | 7/2010 | Walker | |
| 2012/0156398 A1 | 6/2012 | Kim | |
| 2012/0163622 A1 | 6/2012 | Karthik et al. | |
| 2013/0035610 A1* | 2/2013 | Cromwell | G16H 50/70 600/586 |
| 2013/0131532 A1 | 5/2013 | Umana | |
| 2014/0276150 A1 | 9/2014 | Sun et al. | |
| 2015/0011912 A1* | 1/2015 | Matsuoka | A61B 5/4255 600/586 |
| 2015/0073306 A1 | 3/2015 | Abeyratne et al. | |
| 2015/0119758 A1* | 4/2015 | Rogers | A61B 5/7203 600/586 |
| 2015/0157273 A1 | 6/2015 | An et al. | |
| 2016/0089107 A1 | 3/2016 | Cromwell | |
| 2016/0367823 A1 | 12/2016 | Cowan et al. | |
| 2017/0050006 A1 | 2/2017 | Imran et al. | |
| 2017/0340306 A1* | 11/2017 | Spiegel | A61B 7/008 |
| 2018/0078195 A1 | 3/2018 | Sutaria et al. | |
| 2018/0303413 A1 | 10/2018 | Hassan et al. | |
| 2019/0216420 A1* | 7/2019 | Hsu | A61B 7/02 |
| 2019/0374149 A1 | 12/2019 | Wahlberg et al. | |
| 2020/0330066 A1 | 10/2020 | Cromwell | |
| 2021/0000442 A1* | 1/2021 | Marshall | A61B 7/008 |
| 2021/0338154 A1 | 11/2021 | Abeyratne | |

FOREIGN PATENT DOCUMENTS

| | | |
|---|---|---|
| EP | 1956982 | 1/2015 |
| JP | 2008139447 | 6/2008 |
| RU | 2145426 | 2/2000 |
| RU | 2010153388 A | 7/2012 |
| RU | 2539994 C1 | 1/2015 |
| WO | WO-97/36543 | 10/1997 |
| WO | WO-2007/107908 | 9/2007 |
| WO | WO-2007/147049 A2 | 12/2007 |
| WO | WO-2008/063938 | 5/2008 |
| WO | WO-2009/074985 | 6/2009 |
| WO | WO-2011/049293 | 4/2011 |
| WO | WO-2011/130589 | 10/2011 |
| WO | WO-2012/057406 | 5/2012 |
| WO | WO-2012/162740 | 12/2012 |
| WO | WO-2014/039404 | 3/2014 |
| WO | WO-2018/011631 | 1/2018 |
| WO | WO-2019/067880 | 4/2019 |
| WO | WO-2019/241674 | 12/2019 |

OTHER PUBLICATIONS

Dalle et al., "Computer analysis of bowel sounds," Computers in Biology and Medicine, 1974; 4, pp. 257-256.

European Search Report issued in related application No. EP 11769638.5, dated Jul. 18, 2014.

First Examination Report issued by the Intellectual Property Office in India for related Indian Application No. 9563/CHENP/2012, dated Jul. 19, 2019.

Garner et al., "Non-invasive Topographic Analysis of Intestinal Activity in Man on the Basis of Acustic Phenomena," Res Exp Med., 1989; 189; pp. 129-140.

International Search Report and Written Opinion dated Jul. 27, 2020 in International Patent Application No. PCT/US20/28600.

Sugrue et al., "Computerized Phonoenterography: The Clinical Investigation of a New System," Journal of Clinical Gastroenterology, 1994; 18(2): pp. 139-144.

Tomomasa et al., "Analysis of Gastrointestinal Sounds in Infants With Pyloric Stenosis Before and After Pyloromyotomy," [online], Pediatrics, 1999: 104(5), pp. 1-4. Retrieved from the Internet: < URL: http://www.pediatrics.org/cgi/content/full/104/5/e60>, provided by University of Iowa Hospitals on Jan. 1, 2010.

Tomomasa et al., "Gastrointestinal Sounds and Migrating Motor Complex in Fasted Humans," The American Journal of Gastroenterology, 1999; 94(2), pp. 374-381.

Watson et al., "Phonoenterography: the recording and analysis of bowel sounds," Gut, 1967; 8(88); pp. 88-94.

Yong et al., "The study of Intestinal Sound Analyzer," Journal of Electronic Measurement and Instrument, 1995; 9(1), with English language translation, translated by Morningside Translations on Nov. 3, 2014, 14 pages total.

International Search Report and Written Opinion issued in PCT/US2021/036037, dated Sep. 9, 2021.

Search Report issued in Russian Patent Application No. 2021 133 022, dated Aug. 21, 2023.

* cited by examiner

ENHANCED DETECTION AND ANALYSIS OF BIOLOGICAL ACOUSTIC SIGNALS

CROSS-REFERENCE TO RELATED APPLICATIONS

This Application claims the benefit of U.S. Provisional Application 62/834,906 filed on Apr. 16, 2019, the disclosure of which is incorporated herein by reference.

FIELD OF THE INVENTION

The invention generally relates to gastrointestinal conditions and impairments, and more specifically to preventive strategies of the same.

BACKGROUND OF THE INVENTION

Postoperative ileus (POI) is acute paralysis of the GI tract that develops 2-6 days after surgery causing unwanted side-effects such as nausea and vomiting, abdominal pain and distention. This occurs most frequently in gastrointestinal surgery. There is a lack of ability to predict which patients are likely to develop these intestinal issues results in increased incidents of postoperative complications, hospital stays, and readmission rates. There is a further lack of an intestinal audio analysis device and methods that more accurately provide risk level analysis by limiting and/or eliminating ambient noise that causes false data points, wherein the devices and methods are more self-contained.

Thus there remains a need for devices and methods for reducing these issues, wherein healthcare providers are better equipped to reduce hospital stays and readmissions, and avoid exacerbation via more accurate feeding introduction, wherein this is accomplished through improved abilities to acquire more accurate risk level information related to the likelihood of a gastrointestinal impairment occurring in a patient, e.g., post-operative.

SUMMARY OF THE INVENTION

The invention concerns the use of an intestinal audio analysis device for predicting gastrointestinal impairment prior to any clinical signs or symptoms occurring.

In certain embodiments, an intestinal audio analysis device is provided that has a patient interface adapted to attach to a surface of a patient's abdomen for a duration of time post-surgery. The device has a diaphragm that vibrates in response to intestinal sounds to create acoustic pressure waves that amplify intestinal sounds made within a patient's abdomen. This allows audio data related to the intestinal sounds to be collected through an acoustic chamber that receives the amplified sound, which passes to an audio collection device located in or near the acoustic chamber. The intestinal audio analysis device has an exterior housing and internal computer, as well as memory and one or more algorithms for providing instructions to the system to perform the variously required steps to provide accurate collection data and analysis. The one or more algorithms can analyze collected audio data for false signals due to ambient noise, analyze two or more spectral event values over time (e.g., MH4), produce a slope of a linear regression analysis for comparison to a pre-determined slope threshold for making a binary prediction related to likelihood and risk of GII, with the risk conveyed, for example, on a user interface display.

In other embodiments, a method of using the intestinal audio analysis device is provided. In certain embodiments, a method of predicting the likelihood and risk level of GII occurring prior to clinical symptoms. Intestinal sounds are recorded to generate audio data of a patient's intestinal sounds. The audio data is processed to identify certain predictive spectral events (e.g., MH4), and the audio data is analyzed for false signals due to ambient noise. As necessary, certain embodiments provide mitigation for the false signals to ensure acquiring a more accurate total number of identified predictive spectral events for linear regression analysis. The resulting slope of spectral event values over time is used to correlate the slope with likelihood of a gastrointestinal impairment occurring (e.g., post-surgery), and based on the correlation, a user is provided with a risk level based on the likelihood.

The embodiments of the invention provide improved control over ambient noise, which increases accuracy of data used to make correlations upon which predictions of post-surgery GII are made prior to clinical symptoms.

DETAILED DESCRIPTION OF THE DRAWINGS

DETAILED DESCRIPTION

Gastrointestinal impairment (GII) is a common concern following surgical procedures. Disclosed herein are systems and methods for predicting GII based upon the patient's intestinal sounds. As is described below, the disclosed systems and methods identify discrete acoustic spectral events within the intestinal sounds, which can be used to predict subsequent GII, and in some instances, post-operative GII. Those spectral events are good indicators of intestinal tract function and/or dysfunction because the sounds are produced by motor activity within the bowel.

In the following disclosure, various embodiments are described. It is to be understood that those embodiments are mere example implementations of the inventions and that other embodiments are possible. All such other embodiments are intended to fall within the scope of this disclosure.

Certain embodiments comprise a device comprising a housing; a display; a processor; and at least one audio collection device. In certain embodiments, there is a primary audio collection device and a secondary audio collection device. In some embodiments, a primary audio collection device can be attached or inserted into a subject.

Figure 1:
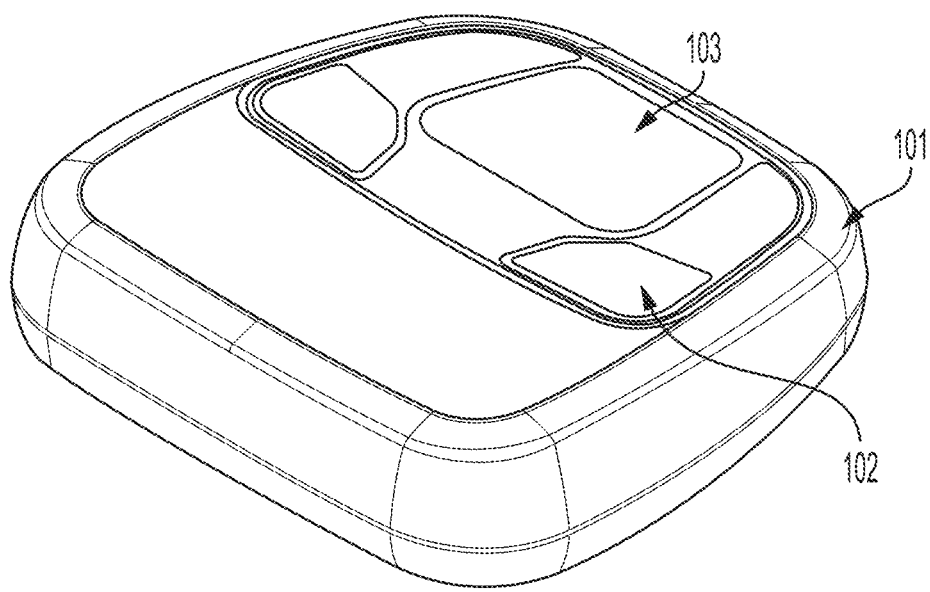
FIG. 1 shows an example of a device as described herein.
Figure 2:
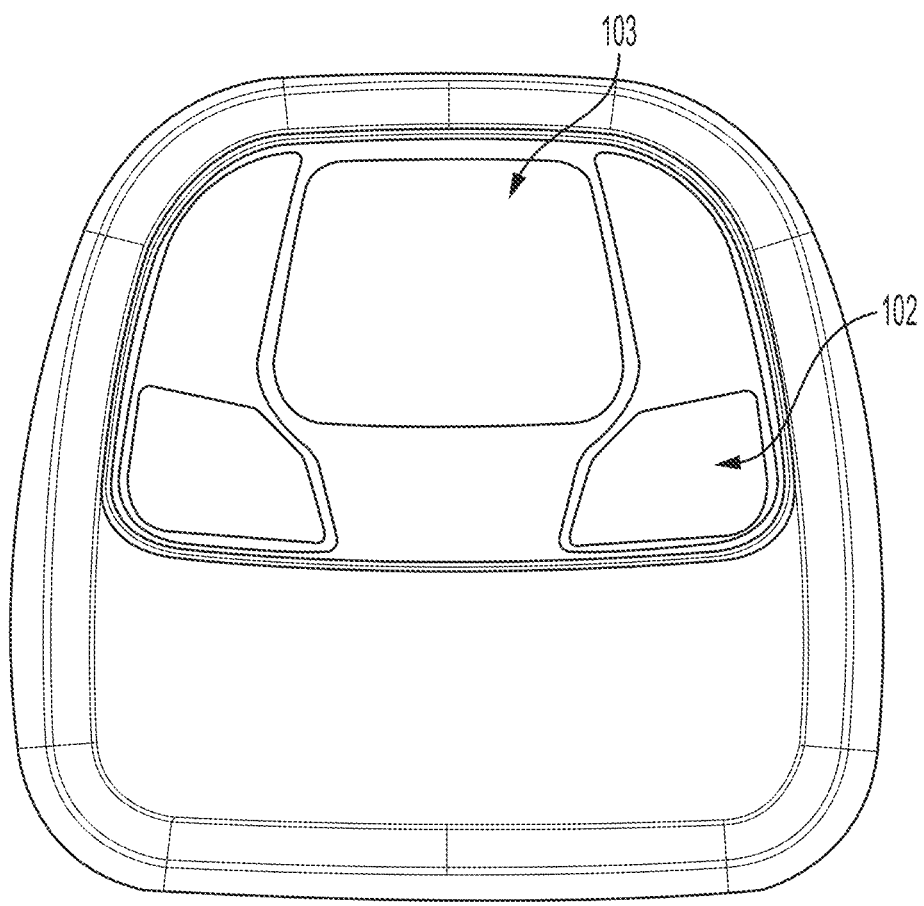
FIG. 2 shows a top view of an example of a device as described herein.

FIGS. 1-2 provide an example of an embodiment of a device. FIG. 1 and FIG. 2 in-part shows an example of a device comprising a housing 101, and at least one button 102 for a user to interact and control the operations of the device, and a user interface 103. A user interface can be a graphical user interface (GUI).

In certain embodiments, a device comprises a secondary audio collection device. In some embodiments, the secondary audio collection device can be a microphone or other sound receiving mechanism that can collect ambient noise. In other embodiments, a signal subtraction is performed of ambient noise from the primary microphone data to achieve true noise cancellation. In some embodiments, devices described herein can be used in methods of predicting or diagnosing GII. In certain embodiments, systems and methods described herein can comprise predicting GII before symptoms have developed. In some instances, a secondary audio collection device can remove interference associated with ambient noise that may interfere with the collection of intestinal sounds. Such a configuration can produce the surprising and unexpected results of more accurately predicting GII. In some instances, the GII prediction can be post-operative. In some embodiments, an ambient audio collection device further comprises a diaphragm.

Figure 3:
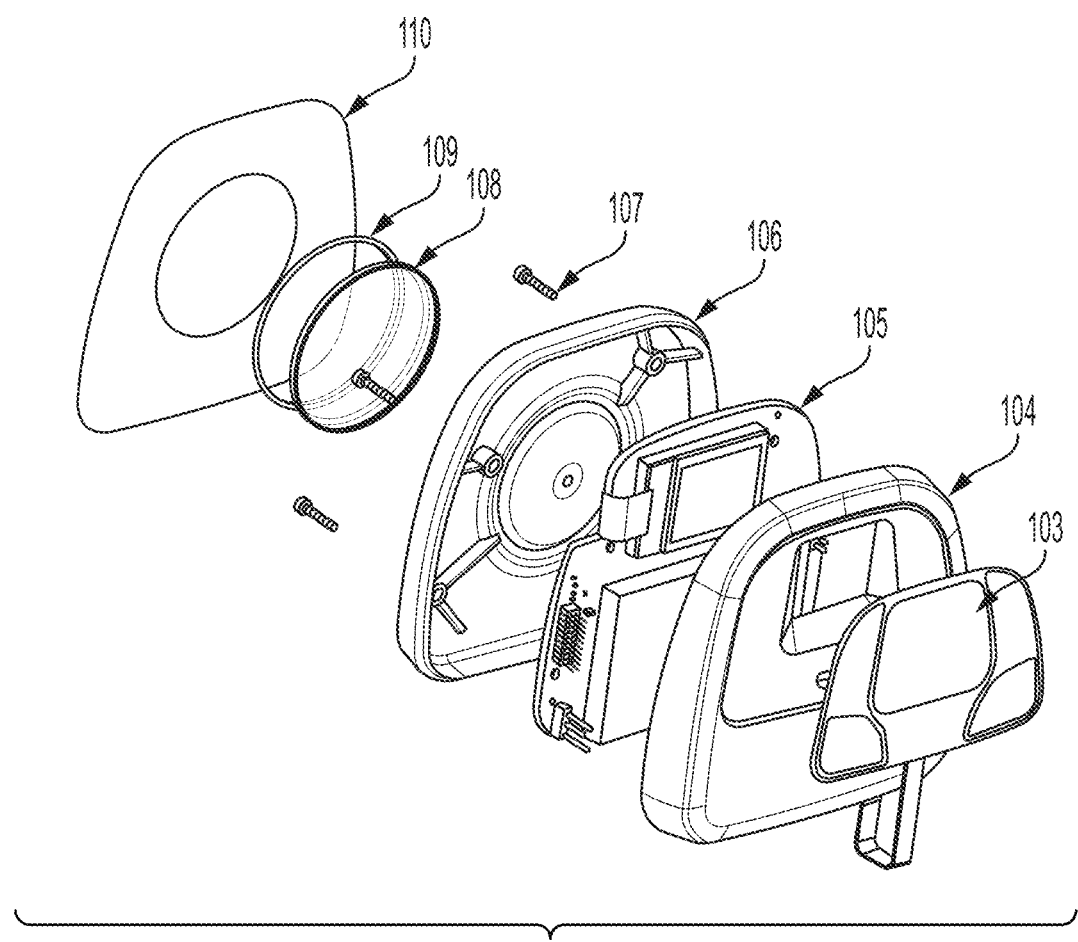
FIG. 3 shows an exploded view of a device as described herein.
Figure 4:
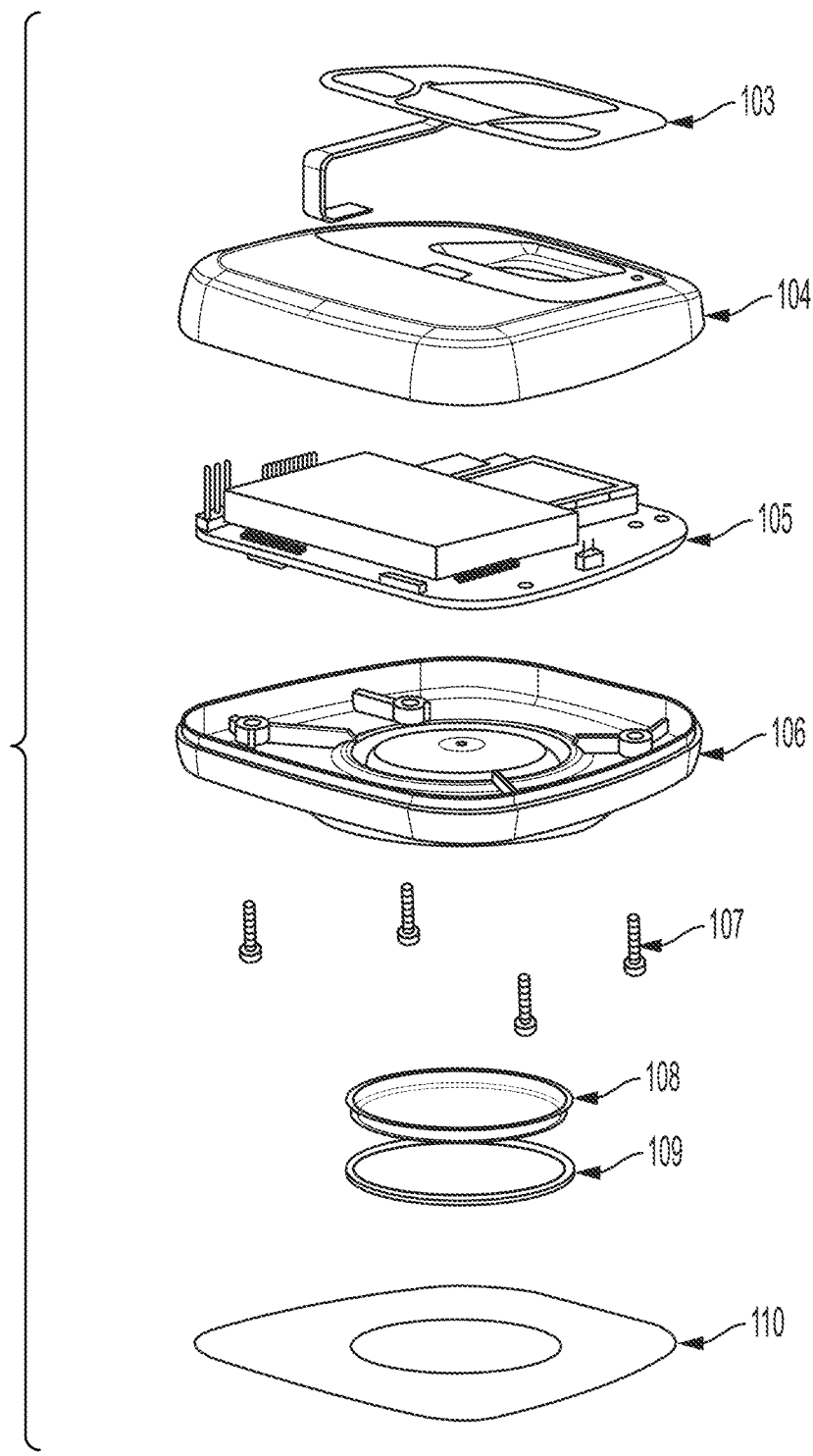
FIG. 4 shows an exploded view of a device as described herein.
Figure 5:
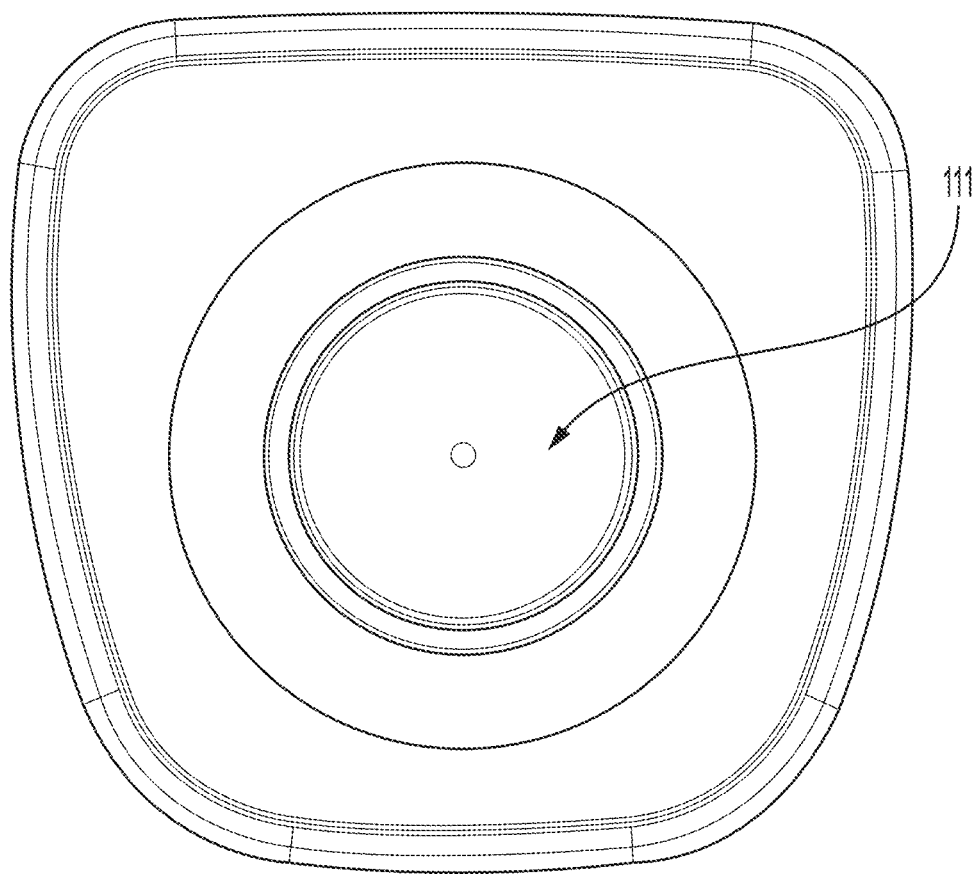
FIG. 5 shows a bottom view of an example of a device as described herein.
Figure 6:
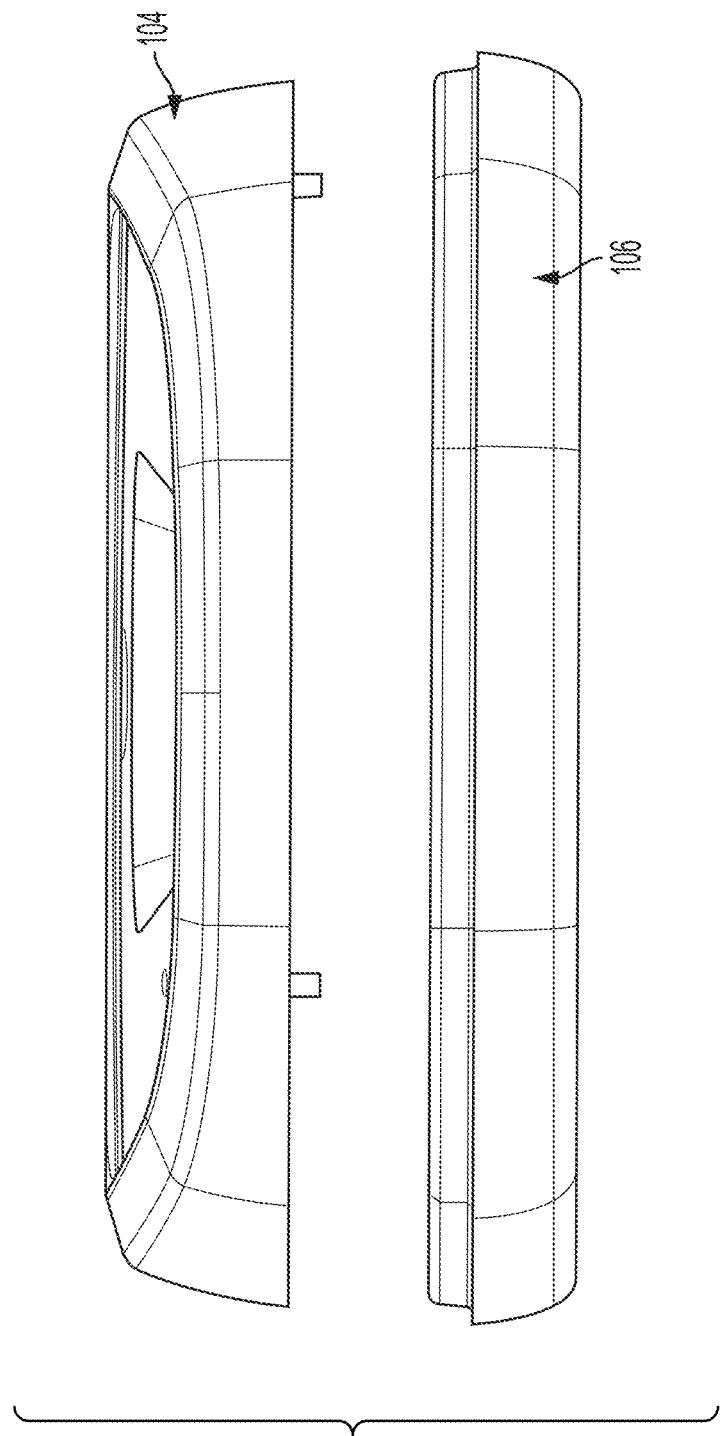
FIG. 6 shows a front view of a separated housing of an example of a device as described herein.
Figure 7:
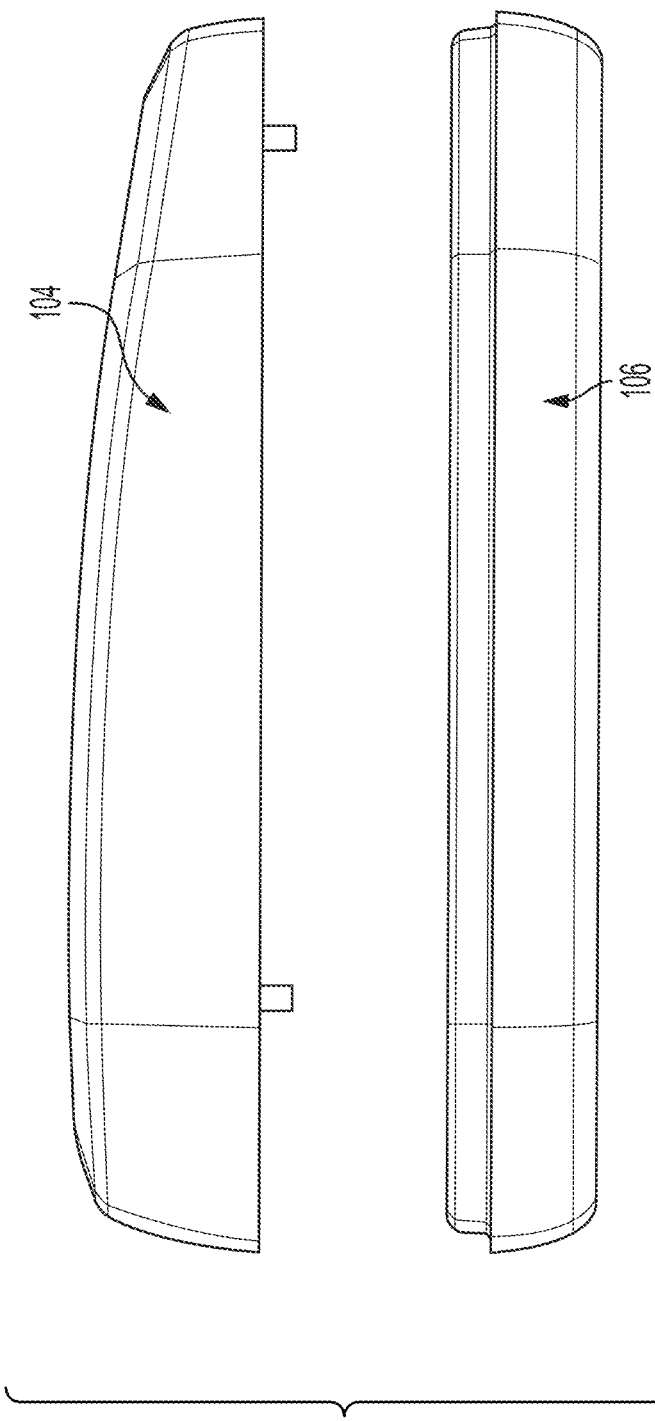
FIG. 7 shows a side view of a separated housing of an example of a device as described herein.

FIGS. 3-4 show an exploded view of an example of a device. FIGS. 3 and 4 show a device comprising a user interface 103, a separable top portion of a housing 104, a computer 105, a lower portion of a housing 106, at least one fastening means 107, a diaphragm 108, a gasket 109, and an adhesive wafer 110. FIG. 5 shows an example of a device having a secondary audio collection device 111.

Figure 8:
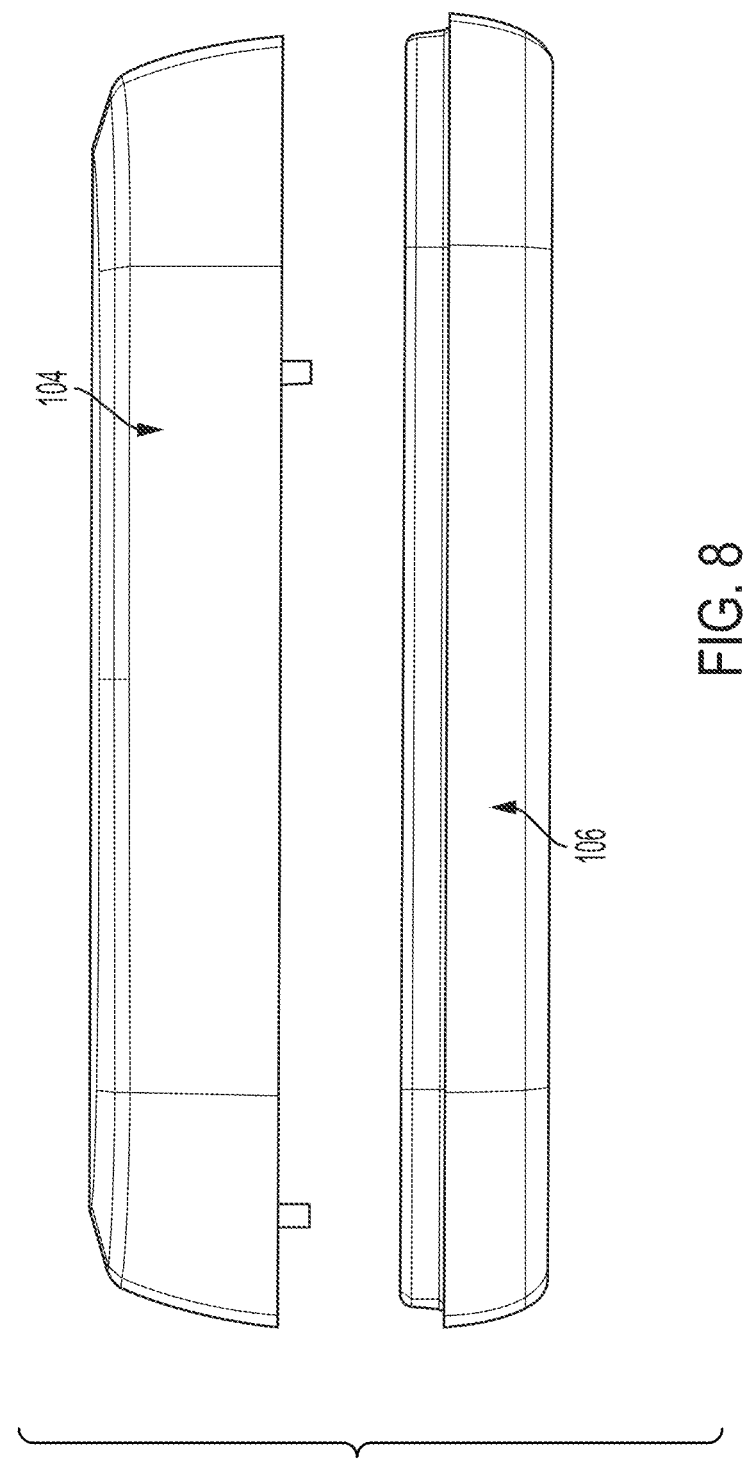
FIG. 8 shows a rear view of a separated housing of an example of a device as described herein.
Figure 9:
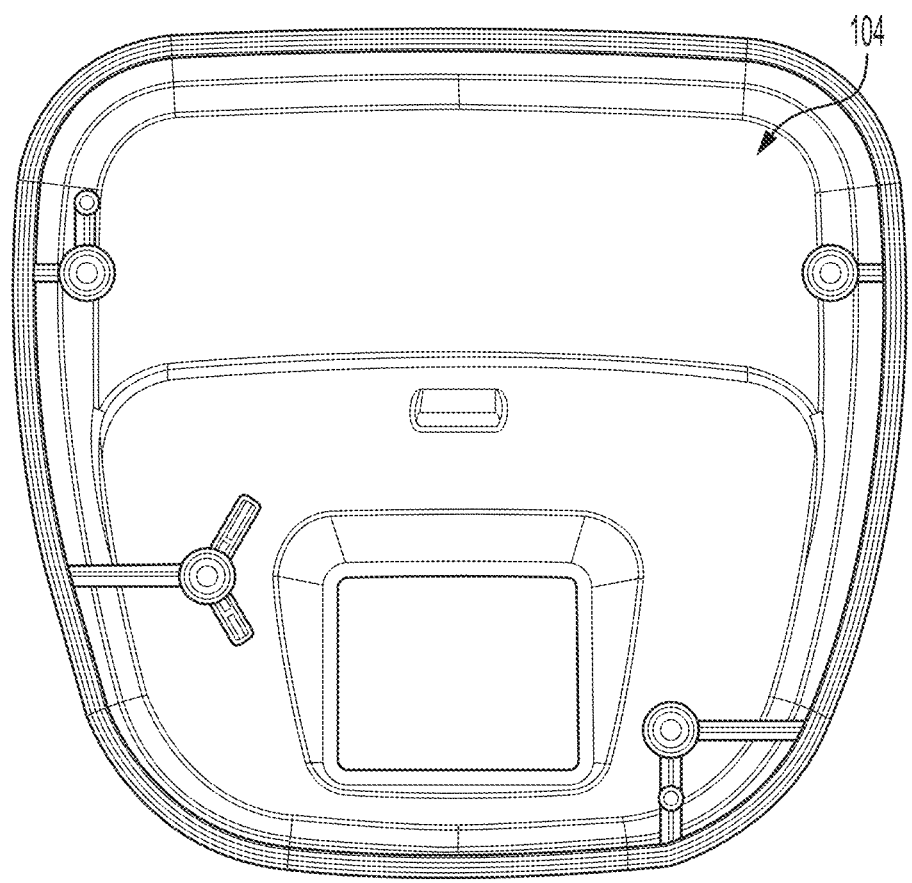
FIG. 9 shows an inside of a top portion of housing without a user interface of an example of a device as described herein.
Figure 10:
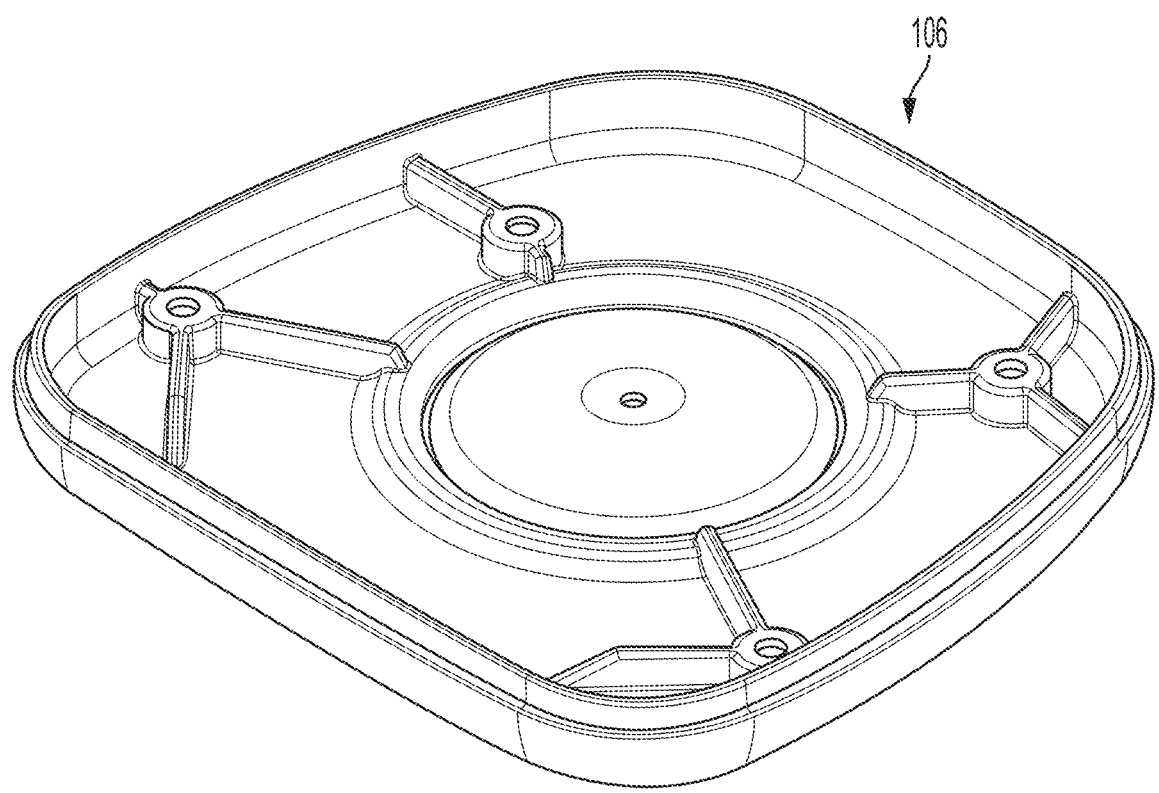
FIG. 10 shows an internal view of a lower portion of a housing of an example of a device as described herein.
Figure 11:
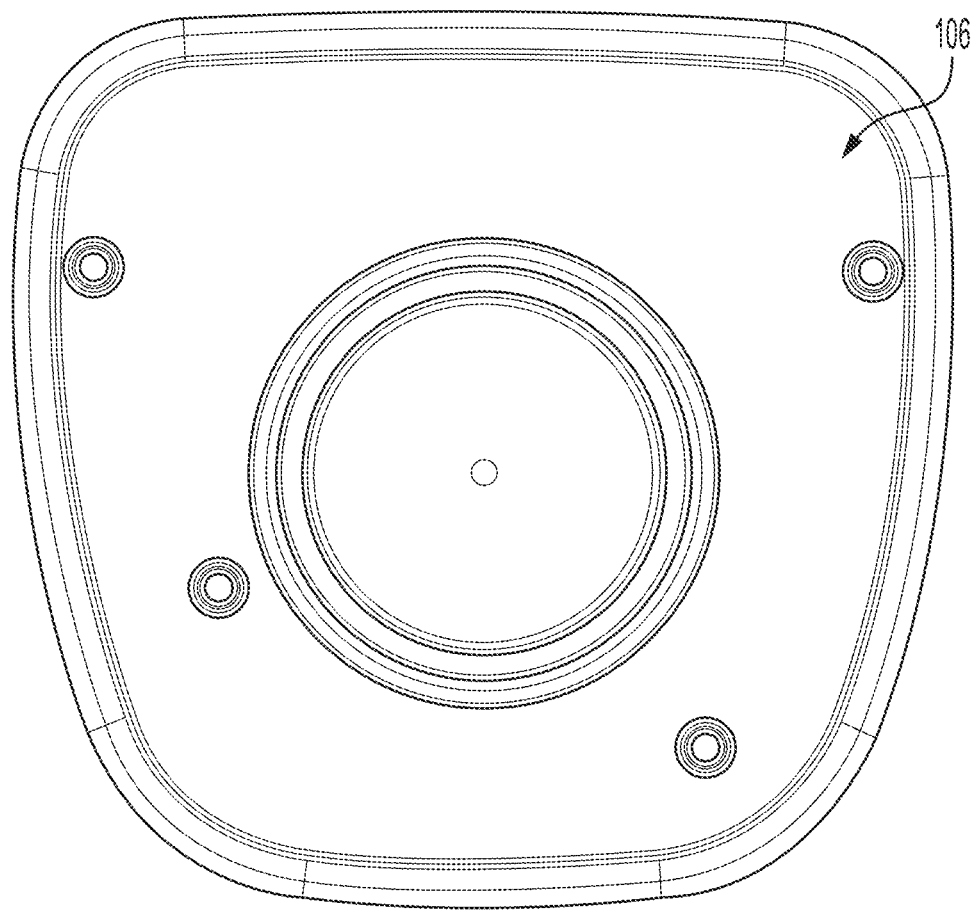
FIG. 11 shows a bottom view of a lower portion of a housing without a secondary audio device and a pedestal of an example of a device as described herein.
Figure 12:
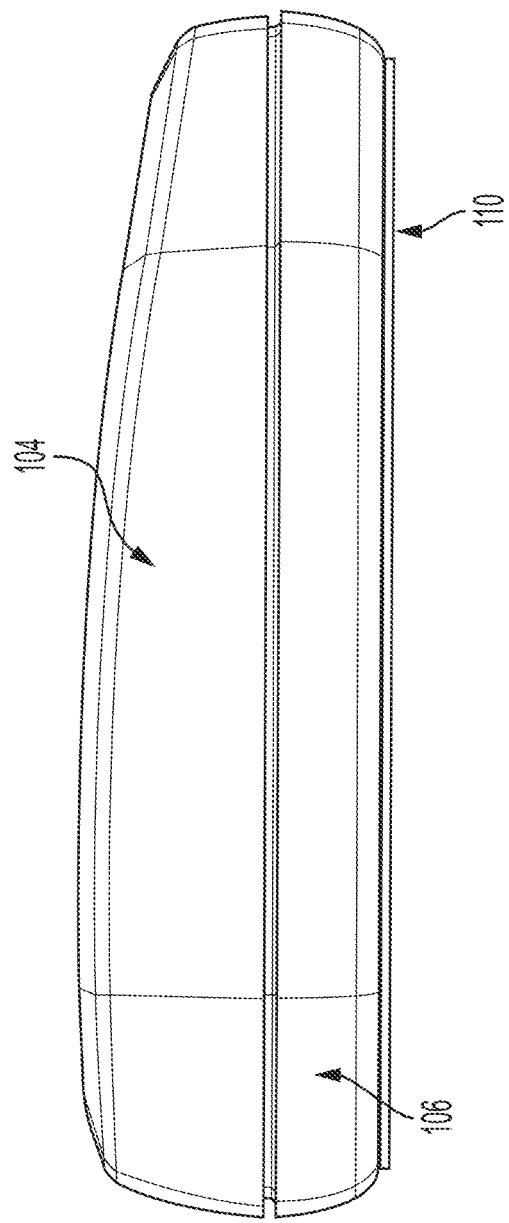
FIG. 12 shows a side view of an example of a device as described herein.
Figure 13:
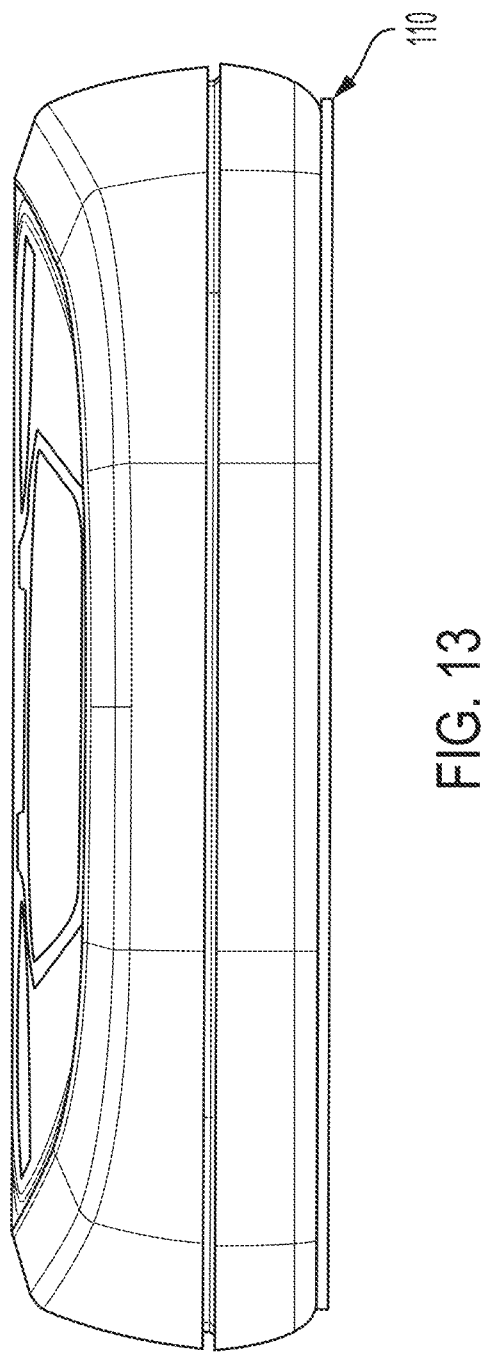
FIG. 13 shows a front view of an example of a device as described herein.
Figure 14:
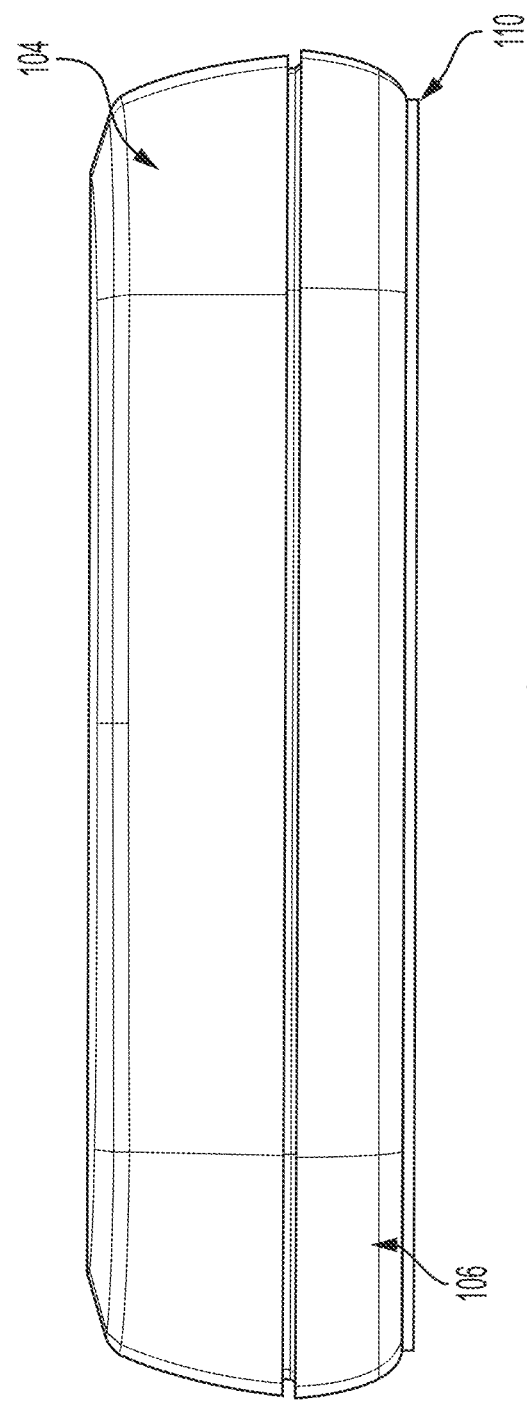
FIG. 14 shows a rear view of a device as described herein.

FIGS. 8-10 show differing views of top portion of a housing 104 and a lower portion of a housing 106. FIG. 9 shows an internal view of top portion of a housing 104, and FIGS. 10-11 show differing views of a lower portion of a housing 106. FIGS. 12-14 show differing views of certain embodiments of a device of the present invention.

A GUI can be configured to allow a user to interact with the device and collect audio data from a subject. Certain embodiments comprise a housing. A housing can comprise an upper portion and an adhesive wafer. The adhesive wafer may range in size (width and length). For example, the wafer may be the same width and length as the bottom surface area of the unit, or smaller than the bottom surface area of the unit. The wafer may be of differing thicknesses. The wafer is shaped to best fit the unit to the patient for a secured monitoring/recording/collecting of GII events. A housing can comprise a separable top portion and lower portion.

In embodiments where a housing comprises a separable top portion and lower portion, the separable top portion and lower portion are secured using attachment means. Attachment means can comprise screws, fasteners, pins, brackets, pegs, rivets, clips, and the like.

An embodiment of a system can be used for predicting gastrointestinal impairment. Embodiments of the system can comprise a data collection device, a patient interface and a computer 105. A computer 105 or a data collection device might be a separate device that collects and/or stores data retrieved from a patient interface and computer 105. A patient interface can comprise any device that is capable of collecting audio data that is generated within a patient's intestinal tract. In some embodiments, the patient interface comprises a portable (e.g., handheld) digital audio recorder. In such a case, the patient interface can comprise an integral microphone (not shown) that is used to capture the intestinal sounds, and wherein an integral microphone can be housed in or near an acoustic chamber. An acoustic chamber can be formed, for example, between a diaphragm 108 and a lower portion of housing 106. The acoustic chamber greatly increases the data collection by amplifying the patient's gut sounds relative to ambient noise; increases the ability to reduce ambient noise at the point of audio collection; provides simplicity in audio data collection through reduction in inventory of extraneous components; and provides the ability of continuous audio data collection in combination with a patient interface, diaphragm and an audio data collection device, e.g., a microphone housed within the device of the invention in or near the acoustic chamber.

A patient interface can be a device that can be directly applied to a patient's abdomen for the purpose of detecting intestinal sounds. In some embodiments, the patient interface comprises, or is similar in design and function to, a stethoscope head. Stethoscope heads can comprise a diaphragm that is placed in contact with the patient and that vibrates in response sounds generated within the body. Those sounds can be delivered to a microphone that can transmit a signal to computer 105, which can optionally transmit data to a data collection device. In some embodiments, a patient interface can transmit sound via tubing that extends between the patient interface and a sound collection device, such as a microphone that can be located within an acoustic chamber. In some embodiments, a patient interface can convert soundwaves into a digital signal that can be processed by computer 105. For example, acoustic pressure waves created by diaphragm vibrations can travel within an inner lumen of tubing to a microphone. In some embodiments, a patient interface can comprise a microphone or other device that converts acoustic pressure waves into a digital signal that can be processed and analyzed by the system to predict GII. As an example, a microphone or other device for converting acoustic pressure waves into digital signals can be housed in or in communication with an acoustic chamber positioned between a diaphragm 108 and a lower portion of housing 106. In some embodiments, all or part of the patient interface can be disposable to avoid cross-contamination between patients. A patient interface can be used with a disposable sheath or cover (not shown) that can be discarded after use.

The audio data collected by the computer 105 can be stored within internal memory comprised by the computer. In some embodiments, memory may be separate from computer 105 but is in data communication with computer 105. In some embodiments, the audio data can be stored within nonvolatile memory (e.g., flash memory) of the device. That data can then be transmitted to computer 105 for processing.

In some embodiments, the data and data analysis are transmitted via a wire or cable that is used to physically connect the computer 105 to a separate processor or computer, such as a laptop or desktop computer or handheld or portable devices with necessary components for receiving and conveying the data and data analysis. In some embodiments, the data and data analysis can be wirelessly transmitted from the device to a separate processor or computer via a suitable wireless protocol, such as Bluetooth or Wi-Fi (IEEE 802.11), or via suitable cellular protocols, such as Global System for Mobile communication (GSM), General Packet Radio Service (GPRS), Enhanced Data Rates for GSM Evolution (EDGE), Universal Mobile Telecommunications Service (UMTS), High Speed Packet Access (HSPA), Code-Division Multiple Access (CDMA), Evolution-Data Optomized (EV-DO, EVDO, 1×EV-DO), Short Message Service (SMS), and Wi-MAX, for example.

The separate computer can, in some embodiments, comprise a desktop computer. It is noted, however, that substantially any computing device that is capable of receiving and processing the audio data collected by the computer 105 can be used. Therefore, a separate computer can, alternatively, take the form of a mobile computer, such as a notebook computer, a tablet computer, a smartphone, or a handheld computer. In some embodiments, computer 105 can process any data produced from acoustic sounds received from a patient and output information via a user interface 103. In some embodiments, a user interface can comprise a display function and can also be a touchscreen that allows a user to interact with and control the operation of the device. For example, the device can be provided with a digital signal processor and appropriate software/firmware that can be used to analyze the collected audio data.

In some embodiments, patient sounds can be transmitted to the device wirelessly from a patient interface. In some embodiments, a patient interface can have an adhesive surface that enables the interface to be temporarily adhered to the patient's skin in similar manner to an electrocardiogram (EKG) lead. In certain embodiments, patient data can be transmitted from a patient interface to computer 105 via a wired connection (via wire or cable) or wirelessly.

In some embodiments, a patient interface can comprise a device having its own integral microphone (not shown) and patient sounds picked up by the microphone can be electronically transmitted along a wire or cable to the device. In some embodiments, the device can comprise a component that is designed to dock with a patient monitoring system, which may be located beside a patient for a continuous period of time, such as hours, days, or weeks. Such patient monitoring systems are currently used to monitor other patient parameters, such as blood pressure and oxygen saturation. For example, a patient monitoring system can comprise a docking station and an associated display. In certain embodiments, this enables a warning or notification to be received at a secondary location, for example, at a nurse's station. The device can also be designed to dock within a free bay of a station prior to use. Other means of connecting a device of the invention is through various ports known in the industry for these types of electronic systems including, for example: PS/2; serial port (e.g., DB-25, DE-9 or RS-232 or COM Port); parallel port or centronics 36 pin port; audio ports; S/PDIF; TOSLINK; video ports; Digital Video Interface (DVI) (e.g., mini-DVI, micro-DVI); display port; RCA connector; component video; S-video; HDMI; USB (e.g., Type A, Type C); RJ-45; RJ-11; e-SATA; and the like. As will be understood, certain adapter for hard connecting the invention to the patient monitoring system is also contemplated. Types of patient monitoring systems are known and include, for example: standard hospital patient monitoring systems for fixed-in place systems as well as mobile and/or portable monitoring systems; remote and/or wireless; home systems; and/or combinations thereof.

In some embodiments, the device may comprise no internal power supply and therefore can only collect patient data when docked. In some embodiments, the device can comprise a power connection such as an A/C connection or can comprise an internal power source such as a battery. In some embodiments, the device can comprise photovoltaic and/or thermoelectric sources of power, such as a solar cell. In some embodiments, a patient interface may comprise a power source such as a battery, photovoltaic device, and/or thermoelectric device that can be used to collect acoustic sound waves and/or process the acoustic sound waves into data that can be used to predict GII. By way of example, the device can have electrical pins that electrically couple the device to a patient monitoring system for purposes of receiving power and transferring collected data to the patient monitoring system. Patient data can be stored in memory of the patient monitoring system and/or can be transmitted to a central computer for storage in association with a patient record in an associated medical records database.

The device can comprise an electrical port that can receive a plug of a wire or cable. In addition, the device can comprise one or more indicators, such as light-emitting diode (LED) indicators that convey information to the operator, such as positive electrical connection with the patient monitoring system and patient signal quality.

The device can couple with a patient monitoring system. In some embodiments, instead of an external patient interface, the device can comprise an internal patient interface that is designed to collect sounds from within the peritoneal cavity. By way of example, the patient interface can comprise a small diameter microphone catheter that is left in place after surgery has been completed, in similar manner to a drainage catheter. Such a patient interface may be particularly useful in cases in which the patient is obese and it is more difficult to obtain high-quality signals from the surface of the skin. To avoid passing current into the patient, the patient interface can comprise a laser microphone. In such a case, a laser beam is directed through the catheter and reflects off a target within the body. The reflected light signal can be received by a receiver that converts the light signal to an audio signal. Minute differences in the distance traveled by the light as it reflects from the target are detected interferometrically. In certain embodiments, a patient interface can comprise a microphone that is positioned at the tip of the catheter.

The device can comprise a central processing unit (CPU) such as computer 105 or other processing device, such as a microprocessor or digital signal processor. The device can comprise memory that can comprise any one of or a combination of volatile memory elements (e.g., RAM) and nonvolatile memory elements (e.g., flash, hard disk, ROM).

A user interface 103 can comprise components with which a user interacts with the device. The user interface 103 can comprise, for example, a keyboard, mouse (mouse pad), interactive touch display, and/or a display device, such as a liquid crystal display (LCD). The device may comprise one or more buttons 102 that can allow a user to use the device and manipulate the user interface 103, such as to navigate through menus, view data, etc. Alternatively or in addition, the user interface 103 can comprise one or more buttons and/or a touch screen. One or more I/O devices can be adapted to facilitate communication with other devices and may include one or more electrical connectors and a wireless transmitter and/or receiver. In addition, in cases in which the device is also collecting and/or processing the data retrieved from a patient, I/O devices can comprise a microphone.

In some embodiments, memory can be a computer-readable medium and can store various programs (i.e., logic), including an operating system and an intestinal sound analyzer. An operating system can control the execution of other programs and can also provide scheduling, input-output control, file and data management, memory management, and communication control and related services. An intestinal sound analyzer can comprise one or more algorithms that are configured to analyze intestinal audio data for the purpose of predicting the likelihood of a patient developing GII. In some embodiments, an analyzer can conduct an analysis relative to correlation data stored in a database (and such database can be stored in computer 105) and can present to the user (e.g., physician, hospital staff and/or clinician) a predictive index of GII risk. In some embodiments, an analyzer can identify particular spectral events of interest using target signal parameters, signal-to-noise ratio parameters, and noise power estimation parameters. Decision tree analysis of the number of predictive spectral events during a specified time interval can then be used to communicate a high-risk, intermediate-risk, or low-risk of GII. In some embodiments, the risk associated with each level of risk is 83%, 30%, and 0%, respectively, or approximately thereabouts.

In certain methods of using the device, patient intestinal sounds can be recorded to generate audio data. As described above, the sounds can be obtained non-invasively, for example using a stethoscope head or other patient interface that is applied to the patient's skin on or near the abdomen. Alternatively, the sounds can be collected with a device that extends into the patient's peritoneal cavity. The sounds can be recorded early in the postoperative period, for example, the day of or a day immediately following surgery, and for any required length of time thereafter. In some embodiments, acoustic sounds are obtained immediately following an operation and may continue being monitored and analyzed for hours, days, or weeks as would be understood by the skilled artisan in view of the instant disclosure. In some embodiments, the sounds are collected continuously. In some embodiments, the sounds are collected for a period of time at a predetermined interval. Regardless of when the sounds are recorded, they can be recorded for a duration of time that is sufficient to enable identification of spectral events that are predictive of intestinal function and/or impairment occurring. By way of example, sounds are recorded for a period of approximately 4 to 6 minutes. In some embodiments, all sounds within the 20-20,000 Hz range are recorded. In some embodiments, sounds outside of the range audible to the human ear are collected and analyzed. Filters can be applied to reduce the range of frequencies that are recorded, and therefore reduce the amount of data that is analyzed. In some embodiments, a secondary audio device 111 can work in conjunction with a patient interface to provide improved analytical results. For example, a secondary audio collection device can comprise a microphone that can measure the ambient noise in the vicinity of a patient. Then, the ambient noise can be subtracted from the acoustic sounds collected from a patient to assure that any acoustic sounds analyzed by the device are actually collected from a patient and not any external source. In certain embodiments, for example, the secondary microphone and the unit's integral microphone collect audio data independently in a synchronized manner. Both sets of audio data are run through the MH4 detector to determine if ambient noise is potentially triggering false MH4 event counts coming from the integral microphone, and wherein the ambient data counts can be subtracted from the final count if certain criteria are met by the ambient sound(s). In some embodiments, filters can be used so that only sounds with frequencies from approximately 700 to 1500 Hz are recorded or analyzed, but a filter can be incorporated that allows the device to only analyze sounds in a predetermined frequency range. As part of mitigating the impact of ambient noise, a warning indicator or alert mechanism can be part of the device, wherein the warning indicator or alert mechanism notifies a doctor, caregiver, nurse or clinician, for example, that an ambient noise(s) must be reduced. There are scenarios where ambient noise levels are too high for the device's noise mitigation strategies to work. In such scenarios, meaningful MH4 values cannot be obtained. A warning indicator, which may be any combination of a light, a noise, audible sound, or a graphic on the device display, can be used to indicate to the user that the ambient noise needs to be reduced and/or controlled. The threshold for triggering the warning indicator can be based, for example, on: a present ambient noise decibel level from an outward-pointing microphone; analysis of the signal/noise ratio from primary versus outward-pointing microphone; processing the sound from the outward-pointing microphone for false-triggering MH4 values above a preset threshold. Although sounds have been described as being "recorded," it will be understood that the sounds can alternatively simply be obtained and real-time processed (as described below) without actually recording the sounds.

Once the audio data is generated, the data can be processed, for example in real-time, to identify one or more predictive spectral signals. Real-time, for example, can mean that data is processed while being acquired via the device as the sounds are generated by the patient. As described above, sounds that are generated by the intestines can be the result of peristalsis, from which the device can predict the likelihood of GII, meaning that device indicates (pre-GII) the likelihood of a GII occurring post-data collection and analysis. Sounds collected and/or analyzed by the device therefore can provide an indication of how the bowels are functioning. For example, paralysis of significant portions of the intestinal tract will proportionally reduce the number of high-energy propulsive contractions in the gut, which results in the loss of some of the higher energy, and thus higher frequency, acoustic spectrum that is typical with normally functioning bowels. As described below, it has been determined that certain predefined spectral events can be identified within the sounds that are highly predictive of whether GII is or is not likely to occur. As is also described below, each of the predefined spectral events is defined by particular characteristics or parameters, such as their frequency, amplitude, duration, and separation in time from other spectral events.

After spectral events have been identified, their number during a specified duration of time (e.g., the total duration of the recording) can be totaled. The totaled number of identified predictive spectral events are time stamped and written to a data buffer (buffer) of a device of the invention. As will be appreciated, the buffer, for example, can be in the physical memory storage used to temporarily store data, while it is understood that a buffer can be in a fixed memory of a hardware or as a virtual data buffer in software pointing at a location in the physical memory. At this point, the total number of spectral events can be compared to correlation data that correlates the number of spectral events with the likelihood of later GII. As an example, a spectral event designated as "MH4" was identified in a study described below. With MH4, a high risk of GII exists if the number of observed MH4 events is less than approximately 21 times during four minutes of recording, an intermediate risk of GII exists if the number of observed MH4 events is greater than approximately 21 but less than approximately 131 times during four minutes of recording, and a low risk of GII exists if the number of observed MH4 events is greater than approximately 131 times during four minutes of recording. The number of predefined spectral events therefore can be used as an index that conveys the magnitude of the risk for GII, with a lower number indicating greater risk and a higher number indicating lower risk.

Once the likelihood of later GII has been determined, that risk can be conveyed to the user. For example, the computer 105 or other device (such as a separate computer) can be used to perform the analysis and can display the risk level on an associated display, such as user interface 103, although the prediction can be shown on a separate display such as a separate computer monitor. In some embodiments, the prediction can be automatically conveyed to a hospital charting and/or recording system so that the prediction is automatically stored with the patient records. In some instance, the data can be anonymized and used as aggregated data. In some embodiments, the risk can be conveyed as an index (i.e., a number). In other embodiments, the risk can be indicated as being "high," "moderate," or "low." Regardless, appropriate action can then be taken relative to the indication and may comprise permitting or prohibiting oral feeding. Notably, further recordings and analysis can be performed on the patient in the ensuing days after surgery to evaluate bowel function and confirm the initial patient assessment.

Any of the features described herein can be combined or substituted as would be understood by the skilled artisan in view of the disclosure and the descriptions provided herein.

As can be appreciated from the above-described method, the risk of GII can be assessed much in the same way that the risk of heart problems can be non-invasively assessed with an EKG. In some embodiments, the risk assessment can be performed in real-time.

A clinical study was performed to evaluate the viability of the disclosed systems and methods. One goal of the study was to confirm that spectral events present in intestinal sounds early in postoperative period do in fact correlate with GII subsequently, before clinical signs and symptoms develop. Another goal of the study was to develop a model for predicting GII that can be implemented as a simple, noninvasive, point-of-care test that will enable hospitals and other institutions to risk stratify patients for development of clinically significant GII using analysis of intestinal sounds.

In the study, patients who were scheduled to undergo inpatient surgery were recruited using an IRB-approved protocol. Patients undergoing abdominal and non-abdominal surgeries were included. Those who were admitted to the ICU postoperatively were excluded from the remainder of the study.

For the study, a device for digitally recording abdominal sounds was assembled using a dual-channel digital audio recorder (Microtrak II, M-Audio Corp., Irwindale, CA), condenser microphone (ATR35s, Audio-Technica Ltd, Leeds, UK), stethoscope tubing, and stethoscope heads. For recording intestinal sounds, the stethoscope heads were applied to the upper and lower anterior abdominal wall and both channels were recorded simultaneously for a period of 5-6 minutes. A standardized tone was also applied to each recording to calibrate audio levels.

Recordings of intestinal sounds were performed by the research team immediately preoperatively and then on each postoperative day. The research team also collected clinical outcome data on a daily basis. Variables related to the development of GII are shown in Table 1. The clinical team providing patient care was blinded to the results of the audio recordings.

TABLE 1

Clinical variables collected daily related to presence of GI 1.

Diet Started
Diet Type
Hours since last meal
Abdominal Distension Present
Emesis
Flatus
Bowel movement
Reversal of diet
Motility agent prescribed
Toleration of diet for 24 h Audio recordings were subsequently processed using digital signal processing algorithms. The algorithms were applied in an iterative fashion focusing on identifying spectral events preoperatively or in the early postoperative period that would predict the development of GII during the remainder of the hospital stay. Five types of spectral events that span different portions of the audible spectrum were ultimately used for the analyses. Each type of spectral event was defined by unique target signal parameters (minimum and maximum frequency, minimum and maximum duration, and minimum separation), signal-to-noise ratio parameters (minimum occupancy, signal-to-noise threshold), and noise power estimation parameters (block size, hop size, percentile). The five spectral events were designated H4, M4, L4, ML4, and MH4, and the parameters for each are shown in Table 2. Spectral events were counted over a four-minute interval of time. GII was defined as the presence of emesis, the need for nasogastric intubation, or the reversal of the diet.

TABLE 2

Detector settings for the defined spectral events.

| | Target Signal Parameters | | | | | Signal-to-Noise Ratio Parameters | | Noise Power Estimation Parameters | | |
| --- | --- | --- | --- | --- | --- | --- | --- | --- | --- | --- |
| Event Name | Min. Freq. (hz) | Max. Freq. (hz) | Min. Dur. (ms) | Max. Dur. | Min. Sep. (ms) | Min. Occupancy (%) | SNR Threshold (dB) | Block Size (ms) | Hop Size (ms) | Percentile (%) |
| L4 | 20 | 400 | 23 | 600 | 11.6 | 66 | 10.0 | 1004 | 499 | 15.0 |
| M4 | 400 | 1400 | 23 | 600 | 29 | 67 | 10.0 | 1497 | 499 | 20.0 |
| H4 | 1400 | 20000 | 5.8 | 600 | 20 | 70 | 10.0 | 1198 | 600 | 20.0 |
| ML4 | 400 | 900 | 5.8 | 600 | 20 | 70 | 10.0 | 1198 | 600 | 20.0 |
| MH4 | 900 | 20000 | 5.8 | 600 | 20 | 70 | 10.0 | 1198 | 600 | 20.0 |

RavenPro 1.4 software was used for visualization, analysis, and measurement of the recorded audio signals. Statistical analyses were performed using PASW 18 and Clementine 10.1.

Thirty-seven patients were recruited into the study. Five patients were excluded due to admission to the ICU postoperatively. Two patients discharged on the day of operation were excluded as no postoperative data was acquired. Of the remaining thirty patients, eleven were male and nineteen were female. The mean age was 52 (SD=12). Five patients had extra-abdominal operations and twenty-five patients had intra-abdominal operations. Nine patients (30% of the total) subsequently developed GII, all within the first four postoperative days. Of those patients, four began on POD1, one on POD2, and four on POD4.

Figure 15:
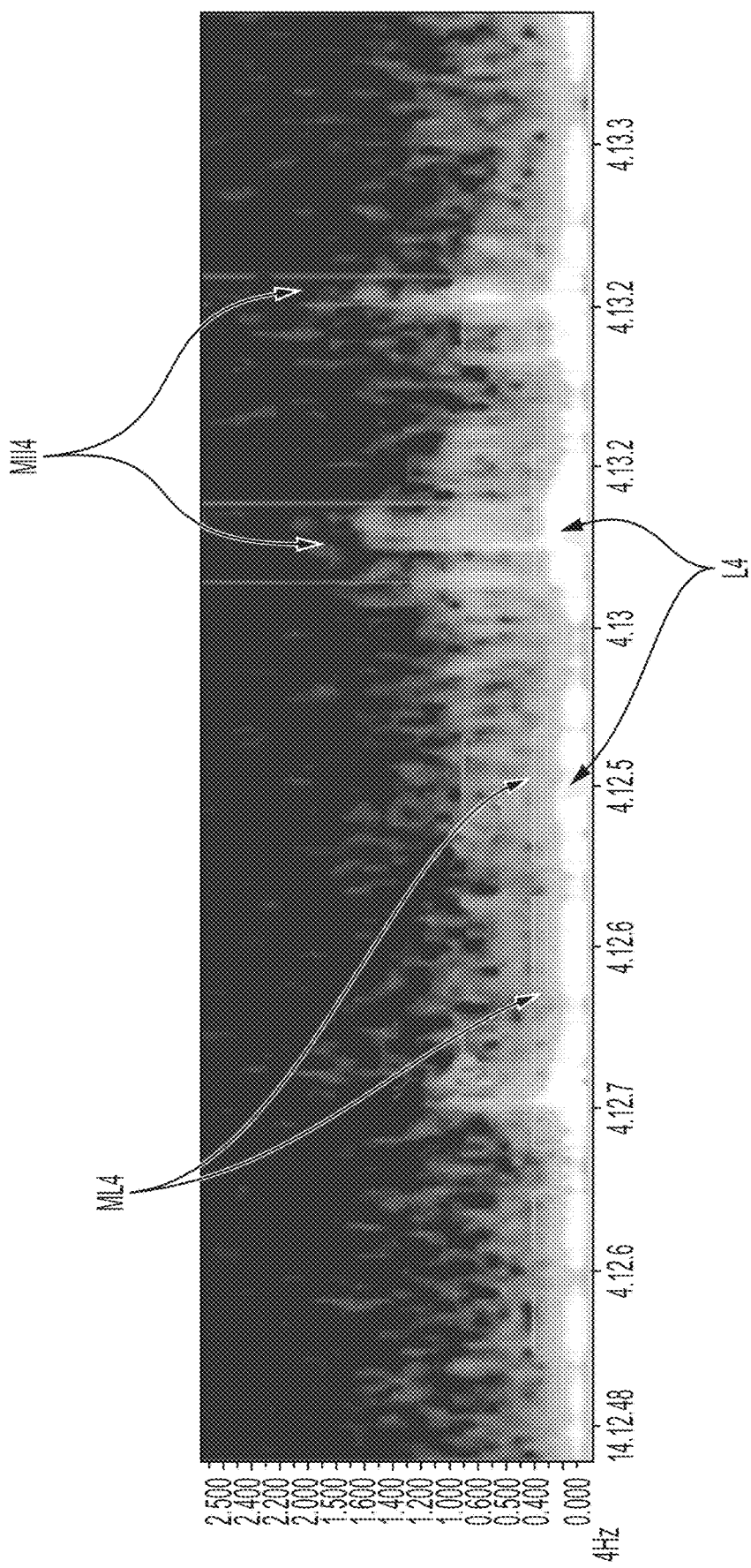
FIG. 15 is an example spectrogram illustrating spectral events contained in recorded abdominal sounds.

Examples of three of the spectral events are shown in a spectrogram of FIG. 15. The mean number of spectral events of each designation was calculated for patients who did or did not subsequently exhibit GII. A two-tailed t-test was then used to assess the significance of any differences. Spectral events obtained from POD0 did not correlate with subsequent development of GII. Spectral events obtained from POD1, however, did prove to correlate with subsequent development of GII. Specifically, MH4 spectral events had a mean count of 154 in patients without subsequent GII and 44 in those who did develop GII (p=0.004).

Figure 16:
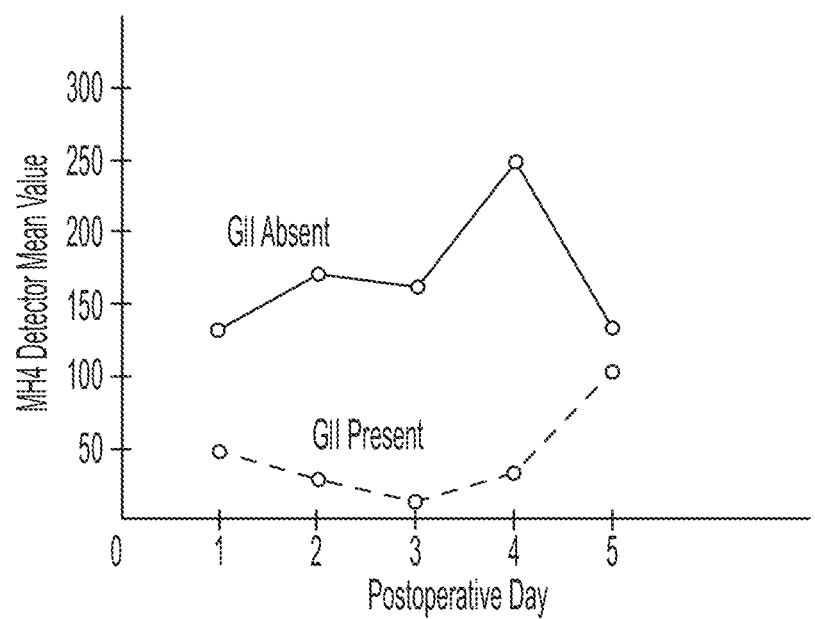
FIG. 16 is a graph that plots temporal changes in a particular spectral event (MH4) in patients with and without gastrointestinal impairment.

FIG. 16 shows an example of a prediction of GII based on the collection of data as described herein and shows a graph that plots temporal changes in MH4 spectral events. The results of the study confirmed that spectral events present in intestinal sounds early in the surgical stay do in fact correlate with GII before clinical signs and symptoms develop. In particular, it was determined that MH4 segregated highly and significantly with the presence of subsequent GII. A predictive model based on MH4 measurement therefore can be used to evaluate patients as being of high-, intermediate-, and low-risk for GII. Significantly, no patients in the low-risk group developed GII. In the study, the predictive value of low-risk classification for no GII was 100%, while the predictive value of high-risk classification for GII was 83%. Thirty percent (30%) of the intermediate-risk patients experienced GII.

Figure 17:
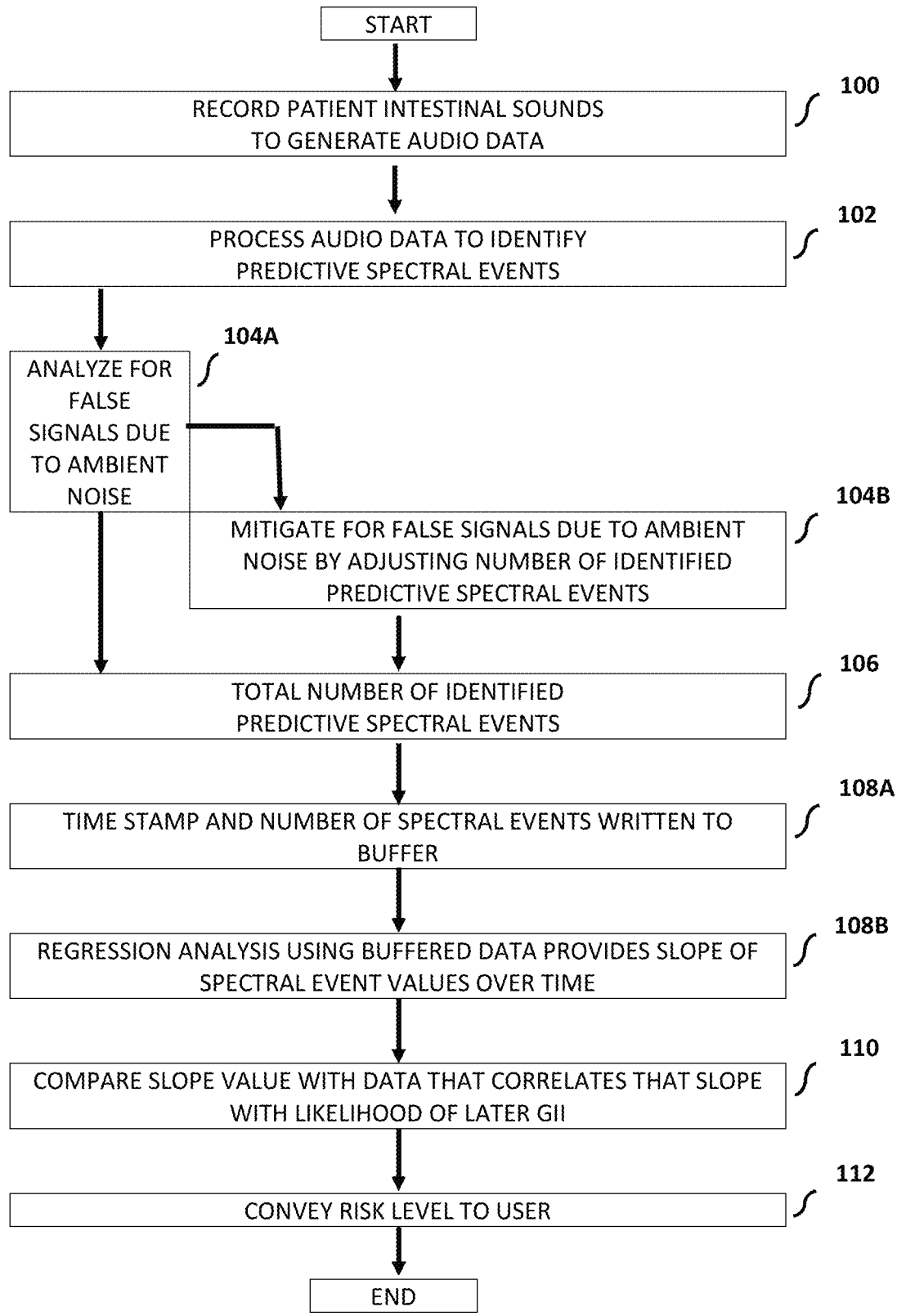
FIG. 17 is a flow diagram of an embodiment of a method for predicting gastrointestinal impairment.

As described here and above for embodiments of the invention, FIG. 17 provides a flow diagram of an embodiment of a method of the invention for predicting GII. As illustrated, once a device of the invention is positioned on the patient, a patient's intestinal sounds are recorded to generate audio data in block 100. As described herein, the sounds can be obtained non-invasively through the patient interface against the patient's skin, at or effectively near the patient's abdomen. The recorded audio data from block 100 is then processed to identify predictive spectral events (e.g., MH4) in block 102. The processed audio data of block 102 is then analyzed for false signals due to ambient noise in block 104A. If a device of the invention does not indicate such false signals are in need of mitigation, then a total number of identified predictive spectral events is computed in block 106. If, however, a device of the present invention detects a threshold-exceeding number of false signals in block 104A, then mitigation of false signals due to ambient noise is performed and the device recalculates by adjusting the number of identified predictive spectral events to account for false signals in block 104B, while alerting/warning the user of a need to reduce or control ambient noise. Once mitigation in block 104B is complete, the total number of identified predictive spectral events is provided in block 106, as described for the non-mitigation determination from block 104A, discussed above. With the total number of identified predictive events calculated in block 106, a time stamp and number of spectral events are written to a buffer in block 108A, and a slope of spectral event values over time is generated from a regression analysis of buffered data in block 108B. Then the slope value is compared to data that correlates the slope with a likelihood of a GII occurring in the future in block 110. This aspect provides a significant improvement over other methods by analyzing the slope of two or more spectral event values (i.e., MH4 values) over time. For example, MH4 values between about 7 to about 12 hours post-surgery are obtained, and the slope of the linear regression analysis of these points is calculated. Rather than a single MH4 value gathered at 12 hours post-surgery serving as the predictor, the calculated slope of the present invention is compared to a pre-determined slope threshold for making a binary prediction. This aspect of the invention corrects for potential erroneous interpretations due to a single MH4 value, which may be falsely elevated by ambient noise interference; however, the present invention provides analysis based on multiple values and results with analysis results that are more resilient to outside interference such as ambient noise. This ability of mitigating false signals greatly increases risk level analysis and strategies, especially when used in a device of the invention comprising an acoustic chamber as herein defined. From the correlation of block 110, a device of the invention indicates a risk level to the user in block 112, for decision making regarding preparation, prevention, treatment and other strategies for addressing the likelihood of a predicted GII event occurring. As discussed herein, devices and methods are provided that allow for real-time data collection, analysis, correlation to provide a result that is predictive of a GII occurring at a particular risk level.

Figure 18:
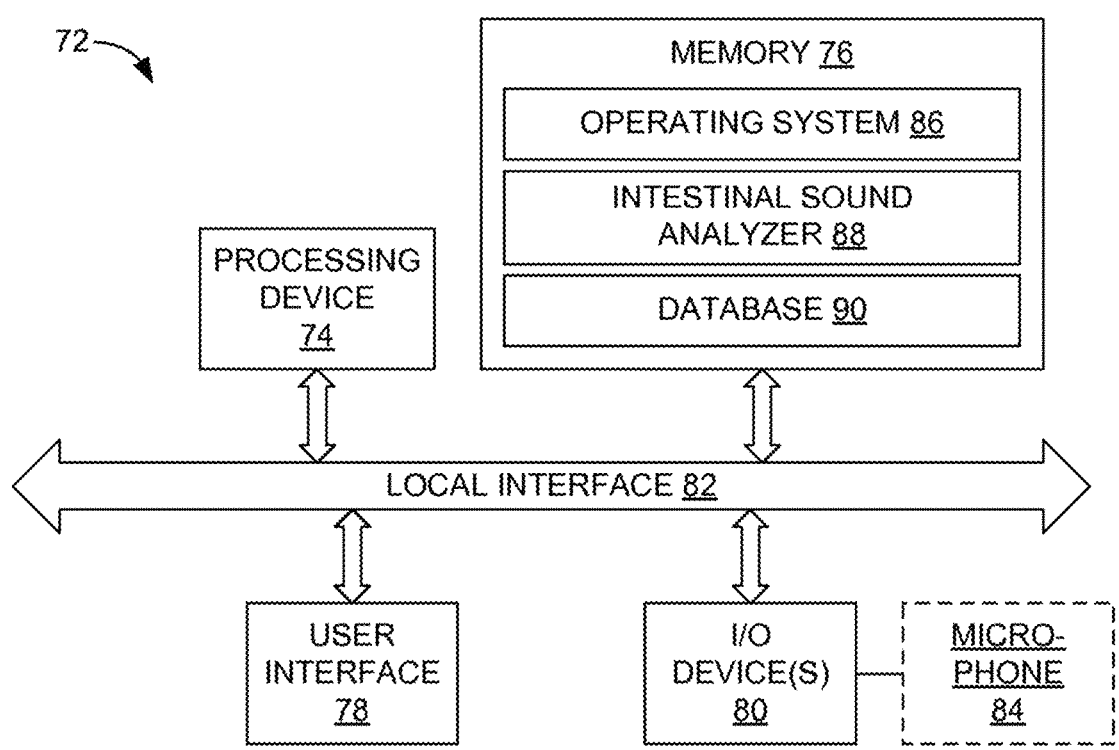
FIG. 18 is a block diagram of an embodiment of an architecture of a device, such as those in FIGS. 1-14, that can process collected patient data to assist in the gastrointestinal impairment prediction and risk assessment.

FIG. 18 illustrates an example architecture for a device 72 that can be used in a system for predicting gastrointestinal impairment to analyze collected patient data. By way of example, the architecture shown in FIG. 18 can be the architecture of a device of the invention comprising the computer 105 and user interface 103 of FIGS. 3-4, for example, as well as the data collection device, processing device, user interface, I/O device(s) (including microphone), memory (including operating system, intestinal sound analyzer, a database, etc.) as described herein. Moreover, it is noted that the illustrated architecture can be distributed across one or more devices.

As is indicated in FIG. 18, the device 72 generally comprises a processing device 74, memory 76, a user interface 78, and input/output devices 80, each of which is coupled to a local interface 82, such as a local bus.

The processing device 74 can include a central processing unit (CPU) or other processing device, such as a microprocessor or digital signal processor. The memory 76 includes any one of or a combination of volatile memory elements (e.g., RAM) and nonvolatile memory elements (e.g., flash, hard disk, ROM).

The user interface 78 comprises the components with which a user interacts with the device 72. The user interface 78 can comprise, for example, a keyboard, mouse, and a display device, such as a liquid crystal display (LCD). Alternatively or in addition, the user interface 78 can comprise one or more buttons and/or a touch screen. The one or more I/O devices 80 are adapted to facilitate communication with other devices and may include one or more electrical connectors and a wireless transmitter and/or receiver. In addition, in cases in which the device 72 is the data collection device, the I/O devices 80 can comprise one or more of microphone 84.

The memory 76 is a computer-readable medium and stores various programs (i.e., logic), including an operating system 86 and an intestinal sound analyzer 88. The operating system 86 controls the execution of other programs and provides scheduling, input-output control, file and data management, memory management, and communication control and related services. The device 72, and preferably memory 86, comprises a data buffer to which time stamped spectral events are written to for analysis via one or more algorithms and/or other software for slope value comparison to data for correlation of slope with likelihood of a later GII, from which risk level is determined. The intestinal sound analyzer 88 comprises one or more algorithms that are configured to analyze intestinal audio data for the purpose of predicting the likelihood of a patient developing GII. In some embodiments, the analyzer 88 conducts that analysis relative to correlation data stored in a database 90 and presents to the user (e.g., physician or hospital staff) a predictive index of GII risk. In some embodiments, the analyzer 88 identifies particular spectral events of interest using target signal parameters, signal-to-noise ratio parameters, and noise power estimation parameters. Decision tree analysis of the number of predictive spectral events during a specified time interval can then be used to communicate a high-, intermediate-, or low-risk of GII. In some embodiments, the risk associated with each level of risk is 83%, 30%, and 0%, respectively, or approximately thereabout.

It is believed that powerful models can be generated from a larger data set of patients and by monitoring intestinal sounds during extended periods of time, such as a 24-hour period. Continuous recording with data averaging and adding additional types of spectral analysis may improve the predictive accuracy of the disclosed technique. Future trials are anticipated that will focus on gathering larger sets of data, validating the proposed predictive model, refining the spectral events analyzed, assessing alternate timings of data collection, and developing widely applicable predictive models. In addition, further development of reliable technology for rapid, point-of-care data continuous acquisition and analysis will be invaluable in expanding these investigations and ultimately in any clinical use. Regardless, the above-described study confirms the feasibility and promise of using acoustic spectral analysis in the study of GII and other gastrointestinal disorders.

Colic is the leading cause of premature death in horses. While colic refers to abdominal pain, it may reflect a number of underlying disorders affecting the large intestine including blockage, spasm, or torsion. Early diagnosis is the key to preventing death; however, early diagnosis in the larger mammals, such as horses is challenging. Because the underlying causes of colic reflect mechanical changes in the intestine, these are recognizable as subtle differences in the types of noise generated from the regular contractions of the intestine.

A device and system of the present invention can be modified to perform audio spectrum analysis of intestinal sounds in a large mammal, such as a horse. In another aspect of the invention, a series of devices can be used to monitor multiple horses at the same or overlapping times, wherein the devices are networked to a gateway device for transmission of data and/or analysis to at least one other receiving system. The device and system would be configured to be attached (i.e., via straps, adhesion, elastic bands, other similar mechanisms and/or combinations thereof) to the body (e.g., torso or abdomen/underbelly) of the horse with the device microphone positioned toward the body. The data collected by the device can be analyzed by the device. The resulting analysis can be accessed and reviewed off of the device as described herein, or the data analysis can be transmitted to a gateway device located, for example, in a barn, animal shelter, field, pasture, or essentially in an area where a gateway device can receive information from the device attached to the horse and transmit that information to a device at another cite for caregivers to review the analysis for deciding necessary action for the horse. The audio spectral analysis algorithms are to be specifically tuned for early identification of spectral events that are predictive of the likelihood of colic beginning to occur or the early stages of colic, and would have a power consumption strategy that allows for weeks up to months of use before changing the device. It should be appreciated that while the ambient noises near and around horses is different from that of a hospital or other places where humans are cared for, the device of the invention can be readily adjusted to account ambient noises near and around a horse. The use of warning indicators relating to notifications and/or alerts of the need to control ambient noises are described herein above.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. An intestinal audio analysis device comprising:
a patient interface adapted to attach to a surface of a patient's abdomen;
a diaphragm adapted to vibrate in response to intestinal sounds to create acoustic pressure waves which amplify the intestinal sounds made within the patient's abdomen;
an acoustic chamber adapted to receive the acoustic pressure waves caused by diaphragm vibrations which amplify the intestinal sounds;
a primary audio collection device located in or near the acoustic chamber;
a secondary audio collection device;
a housing comprising a computer,
wherein the computer, the primary audio collection device, and the secondary audio collection device are contained within the housing;
a memory comprising one or more algorithms,
wherein at least one of the one or more algorithms analyzes collected audio data from the acoustic pressure waves collected by the primary audio collection device for false signals due to ambient noise,
wherein at least one of the one or more algorithms analyzes two or more spectral event values of the collected audio data over time,
wherein, after the collected audio data is analyzed for the false signals, at least one of the one or more algorithms serves to produce a slope of a linear regression analysis of the two or more spectral event values of the collected audio data over time,
wherein the slope of the linear regression analysis is compared to a pre-determined slope threshold so as to make a binary prediction regarding gastrointestinal impairment; and
a user interface comprising a display.

2. The device of claim 1, wherein the display comprises a graphical user interface.

3. The device of claim 1, wherein the device is configured to collect and analyze the audio signals from the patient to predict a likelihood of the gastrointestinal impairment before clinical signs of the gastrointestinal impairment occur.

4. The device of claim 1, wherein the secondary audio collection device comprises an outward-pointing microphone on the housing and configured to collect the ambient noise.

5. The device of claim 1, wherein the secondary audio collection device is configured to collect the ambient noise.

6. The device of claim 1, wherein the patient interface collects acoustic sound waves and at least one of the primary audio collection device and the secondary audio collection device collects the acoustic pressure waves caused by the diaphragm vibrations resulting from the acoustic sound waves vibrating the diaphragm.

7. The device of claim 1, wherein the secondary audio collection device further comprises a second diaphragm.

8. The device of claim 1, wherein the housing further comprises a separable top portion and lower portion.

9. The device of claim 8, wherein the separable top portion and lower portion are secured using attachment means.

10. The device of claim 1, wherein the device comprises a warning indicator for the false signals due to the ambient noise.

11. The device of claim 1, further comprising:
a buffer,
wherein the at least one of the one or more algorithms analyzes the two or more spectral event values of the collected audio data and provides a time stamp and a total number of identified spectral events to the buffer, and
wherein the at least one of the one or more algorithms serves to produce the slope of the linear regression analysis using the buffered data.

12. A method of predicting a likelihood of a gastrointestinal impairment occurring, the method comprising:
recording, with the device of claim 1, the intestinal sounds made within the patient's abdomen to collect the audio data from the acoustic pressure waves collected by the primary audio collection device;
analyzing, with the computer, the collected audio data for the false signals due to the ambient noise;
mitigating, with the computer, for the false signals if the analyzing the collected audio data for the false signals indicates mitigation is necessary;
processing, with the computer, the collected audio data to identify the two or more spectral event values;
acquiring, with the computer, a total number of the identified two or more spectral event values;
performing, with the computer, the linear regression analysis on the processed audio data resulting in the slope of the two or more spectral event values over time;
correlating, with the computer, the slope with the likelihood of the gastrointestinal impairment occurring; and
providing a user with a risk level based on the likelihood on the display.

13. The method of claim 12, wherein the mitigating step comprises adjusting the number of identified predictive spectral events by accounting for the false signals due to ambient noise, resulting in the total number of identified predictive spectral events.

14. The method of claim 12, wherein the performing step comprises providing a time stamp and writing the total number of identified spectral events to a buffer of the device.

15. The method of claim 14, wherein the linear regression analysis is performed using the buffered data.

16. The method of claim 12, wherein the correlating step is performed by comparing the slope with data correlating the slope with the likelihood of a later occurring gastrointestinal impairment.

17. The method of claim 12, wherein the method further comprises a step of warning the user if the analyzing for the false signals indicates that the mitigation is necessary.

18. The method of claim 17, wherein the warning is provided with a warning indicator as part of the device, wherein the warning indicator is selected from a list comprising a light, a noise, a graphic on the display of the user interface, or combinations thereof.

19. The method of claim 17, wherein the warning step is activated by:
1) A preset ambient noise decibel level from the secondary audio collection device;
2) Analysis of a signal-to-noise ratio from the primary audio collection device versus the secondary audio collection device; and
3) Processing the ambient noise received by the secondary audio collection device for false-triggering of a spectral event above a preset threshold.

20. The method of claim 12, wherein one of the two or more spectral event values is MH4.

* * * * *